US010304315B2

(12) United States Patent
Newman et al.

(10) Patent No.: US 10,304,315 B2
(45) Date of Patent: May 28, 2019

(54) SYSTEMS AND METHODS FOR HEALTH MONITORING AND PROVIDING EMERGENCY SUPPORT

(71) Applicant: AMP LLC, Studio City, CA (US)

(72) Inventors: Fredric Mark Newman, Studio City, CA (US); Marsha Jo Newman, Studio City, CA (US)

(73) Assignee: AMP LLC, Studio City, CA (US)

( * ) Notice: Subject to any disclaimer, the term of this patent is extended or adjusted under 35 U.S.C. 154(b) by 0 days.

(21) Appl. No.: 15/618,487

(22) Filed: Jun. 9, 2017

(65) Prior Publication Data
US 2017/0358200 A1 Dec. 14, 2017

Related U.S. Application Data

(60) Provisional application No. 62/348,113, filed on Jun. 9, 2016.

(51) Int. Cl.
| | | |
|---|---|---|
| *G08B 1/08* | (2006.01) | |
| *G08B 25/00* | (2006.01) | |
| *G08B 25/01* | (2006.01) | |
| *A61B 5/00* | (2006.01) | |
| *A61B 5/0205* | (2006.01) | |
| *A61B 5/145* | (2006.01) | |

(52) U.S. Cl.
CPC ............ *G08B 25/001* (2013.01); *A61B 5/746* (2013.01); *G08B 25/016* (2013.01); *A61B 5/02055* (2013.01); *A61B 5/14532* (2013.01); *A61B 5/747* (2013.01)

(58) Field of Classification Search
CPC G08B 25/001; G08B 3/1016; G08B 21/0216; G08B 21/0222; G08B 21/0269; G08B 25/10

USPC ...................................................... 340/539.12
See application file for complete search history.

(56) References Cited

U.S. PATENT DOCUMENTS

| | | | | |
|---|---|---|---|---|
| 2005/0151642 A1* | 7/2005 | Tupler | ................... | G08B 25/08 340/539.18 |
| 2006/0282021 A1* | 12/2006 | DeVaul | ................ | A61B 5/0024 600/595 |
| 2010/0304709 A1* | 12/2010 | Riley | ................... | G08B 25/016 455/404.2 |
| 2012/0223833 A1* | 9/2012 | Thomas | .............. | G06F 19/3418 340/539.12 |

(Continued)

OTHER PUBLICATIONS

International Search Report and Written Opinion for International Patent Application No. PCT/US2018/036935 dated Sep. 20, 2018, 8 pages.

*Primary Examiner* — Zhen Y Wu
(74) *Attorney, Agent, or Firm* — Morgan, Lewis & Bockius LLP

(57) ABSTRACT

Systems and methods for providing a health monitoring and emergency response service are provided. Each element in a plurality of data elements is obtained from a health monitoring device connected to a corresponding subject in a plural of subjects. An alert is triggered through analysis of the data element or manually triggered by the subject or a subject's circle of support. A communication channel is opened between the subject and the members of the circle of support. The subject or one or more members of the circle of support of the subject verifies or rejects the alert. The alert is sent to a remote monitoring alarm center and emergency responders are dispatched.

21 Claims, 9 Drawing Sheets

(56) References Cited

U.S. PATENT DOCUMENTS

| | | | |
|---|---|---|---|
| 2013/0060167 A1* | 3/2013 | Dracup | A61B 5/11 600/595 |
| 2014/0079192 A1* | 3/2014 | Amerling | H04W 4/90 379/45 |
| 2014/0139616 A1* | 5/2014 | Pinter | A61B 5/0008 348/14.08 |
| 2014/0152453 A1* | 6/2014 | Dahl | G08B 25/005 340/686.6 |
| 2014/0273912 A1* | 9/2014 | Peh | H04W 4/90 455/404.1 |
| 2014/0278475 A1* | 9/2014 | Tran | G06F 19/3418 705/2 |
| 2015/0154847 A1* | 6/2015 | Oliver | H04W 4/80 340/686.6 |
| 2015/0161876 A1* | 6/2015 | Castillo | G08B 21/0453 340/539.11 |
| 2015/0206418 A1* | 7/2015 | Hoffman | G08B 25/08 340/539.13 |
| 2015/0257653 A1* | 9/2015 | Hyde | A61B 5/021 600/473 |
| 2015/0279187 A1* | 10/2015 | Kranz | G08B 21/0415 340/539.12 |
| 2016/0038026 A1* | 2/2016 | Yang | A61B 5/1113 340/540 |
| 2016/0042637 A1* | 2/2016 | Cahill | G08B 25/10 701/3 |
| 2016/0071391 A1* | 3/2016 | Chang | G08B 25/016 340/539.12 |

\* cited by examiner

SYSTEMS AND METHODS FOR HEALTH MONITORING AND PROVIDING EMERGENCY SUPPORT

CROSS-REFERENCE TO RELATED APPLICATION

The present application claims priority to U.S. Patent Application No. 62/348,113, filed on Jun. 9, 2016, entitled "A Health Monitoring Emergency Support, Command and Control System," the entire contents of which is hereby incorporated herein for all purposes by this reference.

TECHNICAL FIELD

The present disclosure generally relates to systems and methods for health monitoring and providing emergency support. More particularly, the present disclosure relates to a health monitoring emergency support, command, and control system designed to locally, and remotely through a support group, enable a subject to connect with first responders.

BACKGROUND

In general, a health monitoring emergency system is configured to enable a subject user to quickly connect with emergency services. With twenty-eight percent annual growth rate of baby boomers and an eighty percent chronic disease rate among senior citizens in the United States, emergency support platforms have become a growth industry that services nearly one billion people. However, even as the industry rapidly grows, society still depends on the old status quo options for emergency response.

Conventional emergency support platforms enable a subject to connect with a public-safety answering point (PSAP). Once in contact with the PSAP, emergency services are dispatched to the subject using a predetermined location provided by the subject, or the subject communicates their location to the PSAP.

When a subject is not at a predetermined location or is not capable of communicating with the PSAP the conventional emergency support platforms fail. There exists a need for a subject to communicate their real time location in the event of an emergency.

Another drawback with conventional emergency support platforms is that they do not provide satisfactory ways for a subject to verify or cancel an alert once the alert has been activated. When a false alert is activated, emergency responders waste precious time and resources that could have been allocated to an actual emergency and patient, while the subject is charged for the cost of the emergency dispatch.

Still another drawback with conventional emergency support platforms is that the circle of support (CoS) for a subject has no means for receiving information regarding an emergency or verifying if the emergency is real or not. A subject's circle of support comprises the persons the subject most readily identifies with and whom know the subject's and their medical history best. When a subject is not capable of communicating, the subject's circle of support cannot assist in any fashion using conventional emergency support systems.

Thus, prior to the present disclosure there existed a need for improved emergency support platforms that streamlines the process of dispatching emergency responders, engaging a subject's circle of support, and supplying the emergency responders with critical patient medical information while minimizing or eliminating the number of false calls.

The information disclosed in this background section is only for enhancement of understanding of the general background of the invention and should not be taken as an acknowledgement or any form of suggestion that this information forms the prior art already known to a person skilled in the art.

SUMMARY

Advantageously, the detailed in the present disclosure address the shortcomings in the prior art detailed above.

Various aspects of the present disclosure are directed to providing a health monitoring emergency support, command, and control system.

One aspect of the present disclosure provides a computer system for providing a health monitoring and emergency support service to a plurality of subjects. The computer system comprises a first computer comprising one or more first processors and a first memory. The first memory comprises first non-transitory instructions which, when executed by the one or more first processors, performs a first method. The first method comprises running a monitoring process.

The monitoring process, for each respective subject in a plurality of subjects, polls for a corresponding data element in a plurality of data elements from a corresponding health monitoring device in a plurality of health monitoring devices associated with the respective subject. In some embodiments, the corresponding health monitoring device is implanted in the corresponding subject. In some embodiments, the corresponding health monitoring device is connected to the corresponding subject. In some embodiments, the corresponding health monitoring device is worn by the corresponding subject. In some embodiments, the corresponding health monitoring device is not worn by or implanted in the corresponding subject.

When the respective data element satisfies an alarm trigger condition, a first notification process for a candidate subject in the plurality of subjects is initiated.

The first notification process, performed for the candidate subject in the plurality of subjects when the respective data element satisfies the alarm trigger condition, comprises creating a communication channel between the candidate subject and the support members in the plurality of support members independent of a location of the support member responsive to the alarm trigger condition. Next, the data element or the alarm trigger condition is communicated to each remote device in a plurality of remote devices and the candidate subject's device. Each remote device in the plurality of remote devices is associated with a respective support member, in a plurality of support members, uniquely associated with the candidate subject. A verification response from any one or more support members in the plurality of support members uniquely associated with the candidate subject is received. Responsive to the verification response, a second notification process is initiated. The second notification process notifies a remote alarm monitoring center about the alarm trigger condition when the verification response satisfies a first condition. The first notification process can be terminated when the verification response satisfies a second condition without notifying the remote alarm monitoring center about the alarm trigger condition.

In some embodiments, the corresponding health monitoring device is a smart phone device. In some embodiments, the corresponding health monitoring device wirelessly transmits the respective data element to the computer system.

In some embodiments, the polling further comprises instructions for receiving an interrupt communication from the candidate subject, so that when the interrupt communication from the candidate subject is received within a predetermined time period of receiving the respective data element for the candidate subject, the first notification process and the alarm trigger condition are cancelled. In some embodiments, the predetermined time period is 15 seconds, 10 seconds, between 5 and 30 seconds, or some other suitable time.

In some embodiments, the respective data element is inputted by the candidate subject using a push command at the health monitoring device associated with the candidate subject. That is, the candidate subject proactively initiates the alarm.

In some embodiments, the respective data element is armed then input through a series of push commands by the candidate subject at the health monitoring device associated with the candidate subject.

In some embodiments, the respective data element includes global positioning system coordinates of the candidate subject and the communicating of the data element or the alarm trigger condition to each remote device in a plurality of remote devices includes communicating the global positioning system coordinates of the candidate subject.

In some embodiments, the respective data element comprises recorded audio or video from the health monitoring device corresponding to the candidate subject, and the communicating the data element or the alarm trigger condition to each remote device in the plurality of remote devices includes communicating the recorded audio or video of the candidate subject.

In some embodiments, the respective data element comprises live audio or video from the health monitoring device corresponding to the candidate subject, and the communicating of the data element or the alarm trigger condition to each remote device in the plurality of remote devices includes communicating the live audio or video of the candidate subject.

In some embodiments, the communicating of the data element or the alarm trigger condition to each remote device in the plurality of remote devices occurs on a recurring basis.

In some embodiments, the communicating of the data element or the alarm trigger condition to each remote device in the plurality of remote devices occurs on the recurring basis at a predetermined interval.

In some embodiments, the respective data element satisfies the alarm trigger condition when the respective data element comprises an audible alarm transmitted through the corresponding health monitoring device associated with the candidate subject.

In some embodiments, the plurality of support members uniquely associated with the candidate subject comprises a family member of the candidate subject or a friend of the candidate subject.

In some embodiments, each support member, in the plurality of support members, serves as a recipient of the data element or the alarm trigger condition on a voluntary basis.

In some embodiments, the remote alarm company is a physician, a provider group, a hospital, a hospital network, a health insurance company, a pharmacy, a governmental body, a first responder business entity, or a prescribing clinician that receives the alarm trigger condition in the second notification process on a subscription basis with the candidate subject.

In some embodiments, the first condition is validation by a respective support member of the need for emergency services for the candidate subject responsive to the communication of the data element or the alarm trigger condition, and the second condition is affirmative validation by a respective support member of the absence of a need for emergency services for the candidate subject responsive to the communication of the data element or the alarm trigger condition.

Another aspect of the present disclosure provides a method for providing a health monitoring and emergency support service to a plurality of subjects. The method comprises running a monitoring process. In the monitoring process, for each respective subject in a plurality of subjects, the monitoring process comprises polling for a respective data element in a plurality of data elements from a corresponding health monitoring device in a plurality of health monitoring devices associated with the respective subject. When the respective data element satisfies an alarm trigger condition, a first notification process for a candidate subject in the plurality of subjects is initiated. The first notification process, performed for the candidate subject in the plurality of subjects when the respective data element satisfies the alarm trigger condition, comprises creating a communication channel between the candidate subject and the support members in the plurality of support members independent of a location of the support member responsive to the alarm trigger condition. Next, the data element or the alarm trigger condition is communicated to each remote device in a plurality of remote devices and the candidate subject's device. Each remote device in the plurality of remote devices is associated with a respective support member, in a plurality of support members, uniquely associated with the candidate subject. A verification response from any one or more support members in the plurality of support members uniquely associated with the candidate subject is received. Responsive to the verification response, a second notification process is initiated. The second notification process notifies a remote alarm monitoring center about the alarm trigger condition when the verification response satisfies a first condition. The first notification process can be terminated when the verification response satisfies a second condition without notifying the remote alarm monitoring center about the alarm trigger condition.

Another aspect of the present disclosure provides a non-transitory computer readable storage medium, where the non-transitory computer readable storage medium stores instructions, which when executed by a computer system, cause the computer system to perform any of the methods for providing a health monitoring and emergency support service described in the present disclosure.

In accordance with an aspect of the present disclosure, the above and other objects can be accomplished by the provision of a health monitoring and emergency support service which streamlines the process of dispatching emergency responders and engages a subject's circle of support.

The methods and apparatuses of the present disclosure have other features and advantages which will be apparent from or are set forth in more detail in the accompanying drawings, which are incorporated herein, and the following Detailed Description, which together serve to explain certain principles of the present invention.

Figure 1:
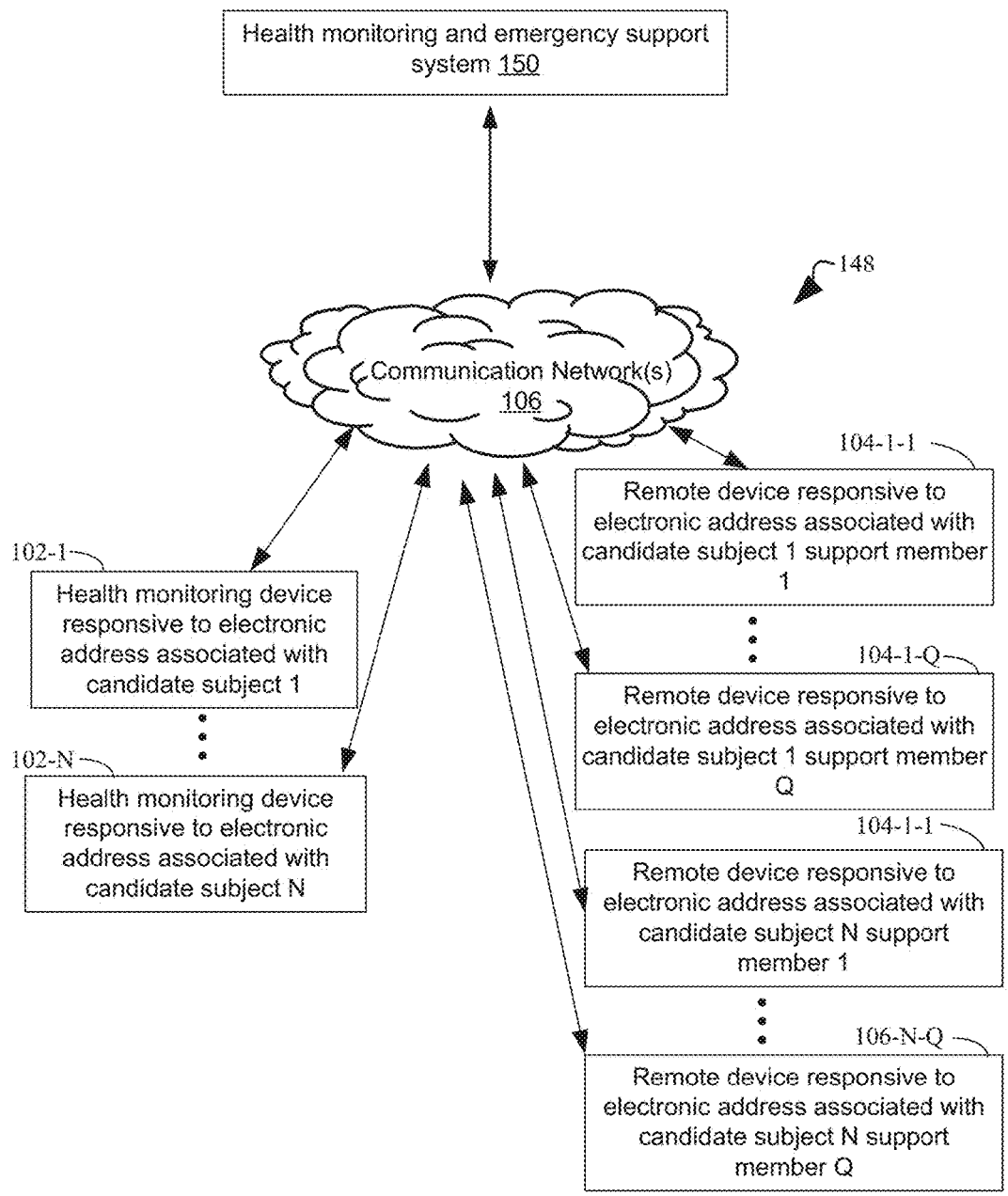
FIG. 1 illustrated an exemplary system topology that includes a health monitoring and emergency support system according to an exemplary embodiment of the present disclosure.

It should be understood that the appended drawings are not necessarily to scale, presenting a somewhat simplified representation of various features illustrative of the basic principles of the invention. The specific design features of the present invention as disclosed herein, including, for example, specific dimensions, orientations, locations, and shapes will be determined in part by the particular intended application and use environment.

In the figures, reference numbers refer to the same or equivalent parts of the present invention throughout the several figures of the drawing.

DETAILED DESCRIPTION

Reference will now be made in detail to various embodiments of the present disclosure, examples of which are illustrated in the accompanying drawing and described below. While the disclosure will be described in conjunction with exemplary embodiments, it will be understood that the present description is not intended to limit the invention(s) to those exemplary embodiments. On the contrary, the invention(s) is/are intended to cover not only the exemplary embodiments, but also various alternatives, modifications, equivalents and other embodiments, which may be included within the spirit and scope of the present invention as defined by the appended claims.

It will also be understood that, although the terms first, second, etc. may be used herein to describe various elements, these elements should not be limited by these terms. These terms are only used to distinguish one element from another. For example, a first subject could be termed a second subject, and, similarly, a second subject could be termed a first subject, without departing from the scope of the present disclosure. The first subject and the second subject are both subjects, but they are not the same subject. Furthermore, the terms "subject" and "user" are used interchangeably herein.

The terminology used in the present disclosure is for the purpose of describing particular embodiments only and is not intended to be limiting of the invention. As used in the description of the invention and the appended claims, the singular forms "a", "an" and "the" are intended to include the plural forms as well, unless the context clearly indicates otherwise. It will also be understood that the term "and/or" as used herein refers to and encompasses any and all possible combinations of one or more of the associated listed items. It will be further understood that the terms "comprises" and or "comprising," when used in this specification, specify the presence of stated features, integers, steps, operations, elements, and or components, but do not preclude the presence or addition of one or more other features, integers, steps, operations, elements, components, and/or groups thereof.

As used herein, the term "if" may be construed to mean "when" or "upon" or "in response to determining" or "in response to detecting," depending on the context. Similarly, the phrase "if it is determined" or "if [a stated condition or event] is detected" may be construed to mean "upon determining" or "in response to determining" or "upon detecting [the stated condition or event]" or "in response to detecting [the stated condition or event]," depending on the context.

An aspect of the present disclosure is directed to provide a health monitoring and emergency support service.

The present disclosure relies upon the acquisition of a plurality of data elements, where each data element in the plurality of data elements is from a corresponding health monitoring device of a corresponding subject in a first plurality of subjects. In some embodiments, the corresponding health monitoring device is implanted in the corresponding subject. In another embodiment, the corresponding health monitoring device is worn by corresponding subject. In a further embodiment, the corresponding health monitoring device is not worn by or implanted in the corresponding subject. FIG. 1 illustrates an example of an integrated system 148 for the acquisition of such data. The integrated system 148 includes one or more health monitoring devices 102, each associated with a different subject, one or more remote devices 104, each associated with a different support member, and a health monitoring and emergency support server 150.

In the present embodiment, the health monitoring device 102 and the remote device 104 utilize the same hardware and can be considered the same. Unless stated otherwise, the hardware features of the health monitoring device 102 are the same for the remote device 104.

With the integrated system 148, data elements from the medical devices 102 of subjects are obtained. Each data element comprises a condition of the health monitoring device or a condition of the corresponding subject measured by the health monitoring device. The plurality of data elements are used to determine when an alert is triggered.

Figure 2A:
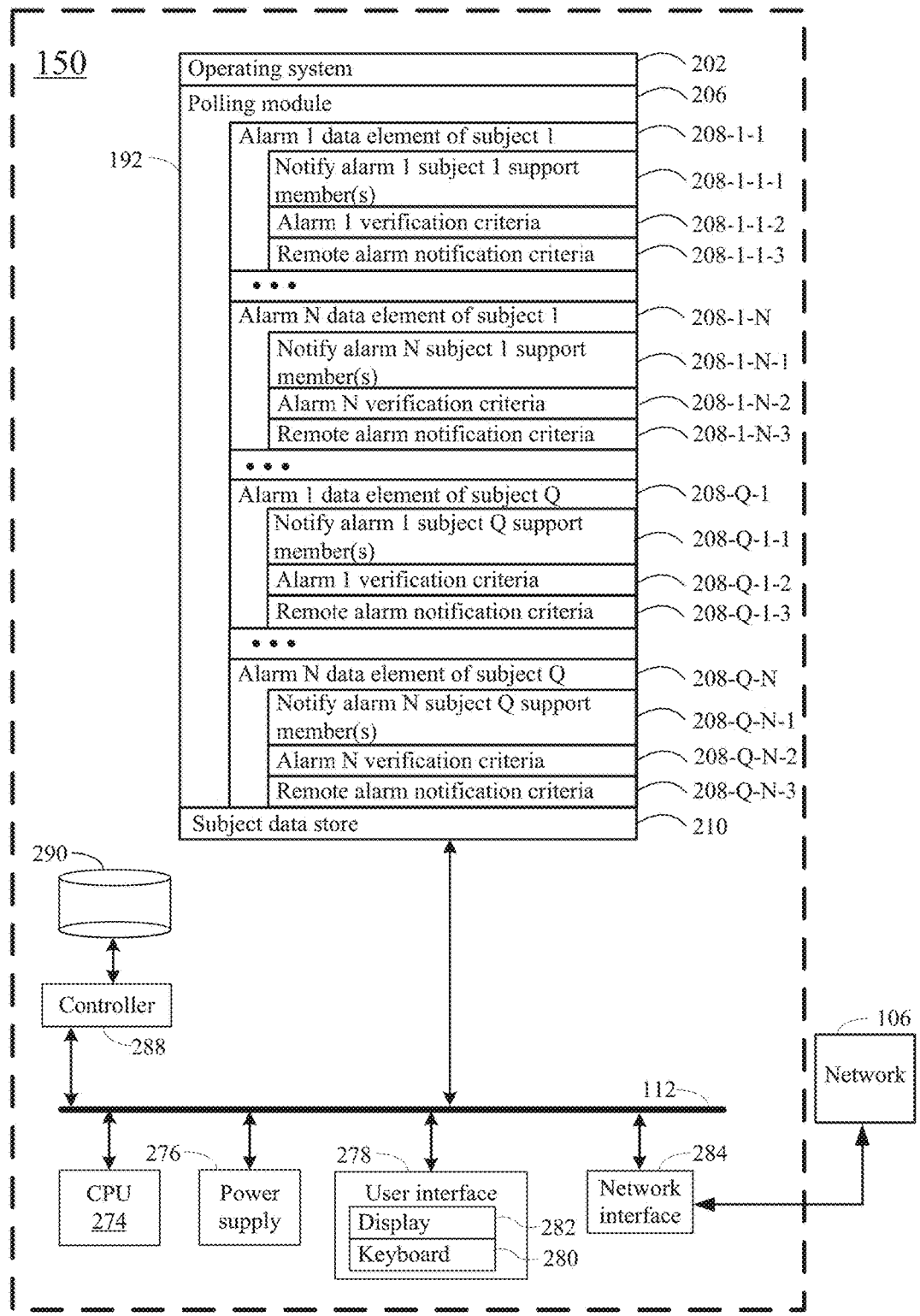
FIG. 2A to FIG. 2B illustrates a health monitoring emergency support system according to an exemplary embodiment of the present disclosure.
Figure 2B:
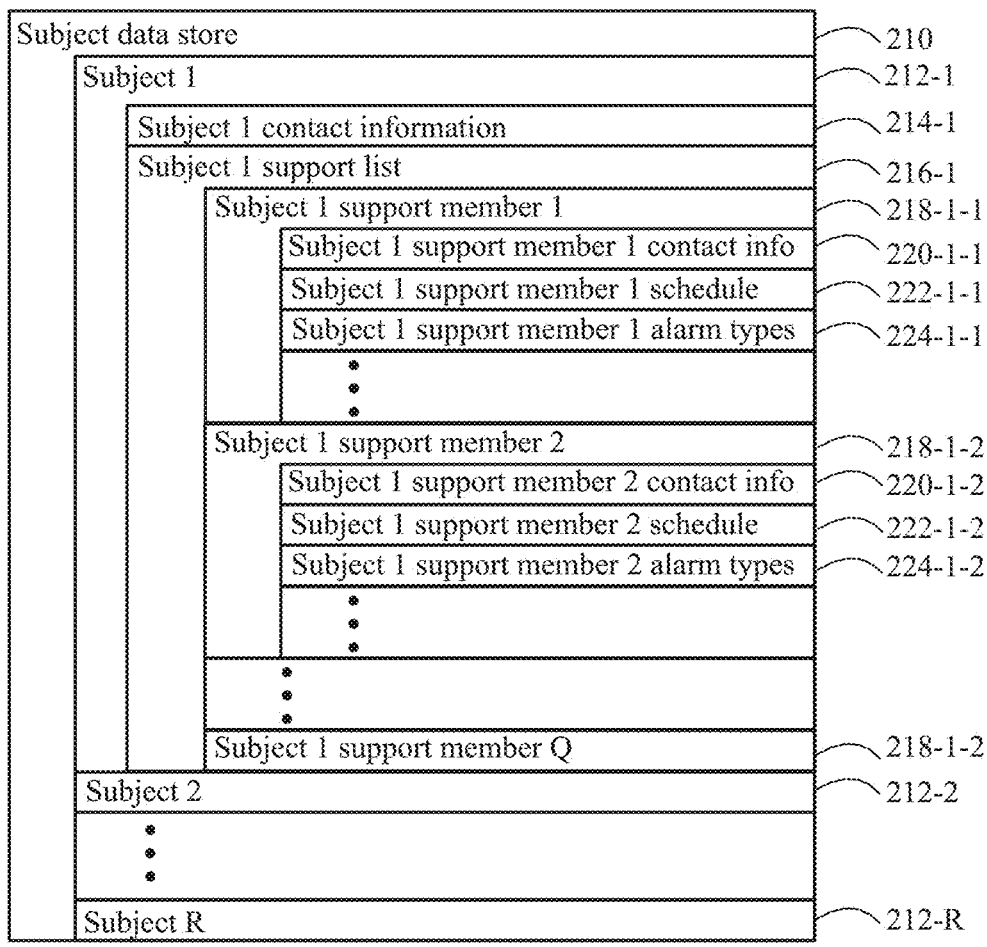
Figure 3:
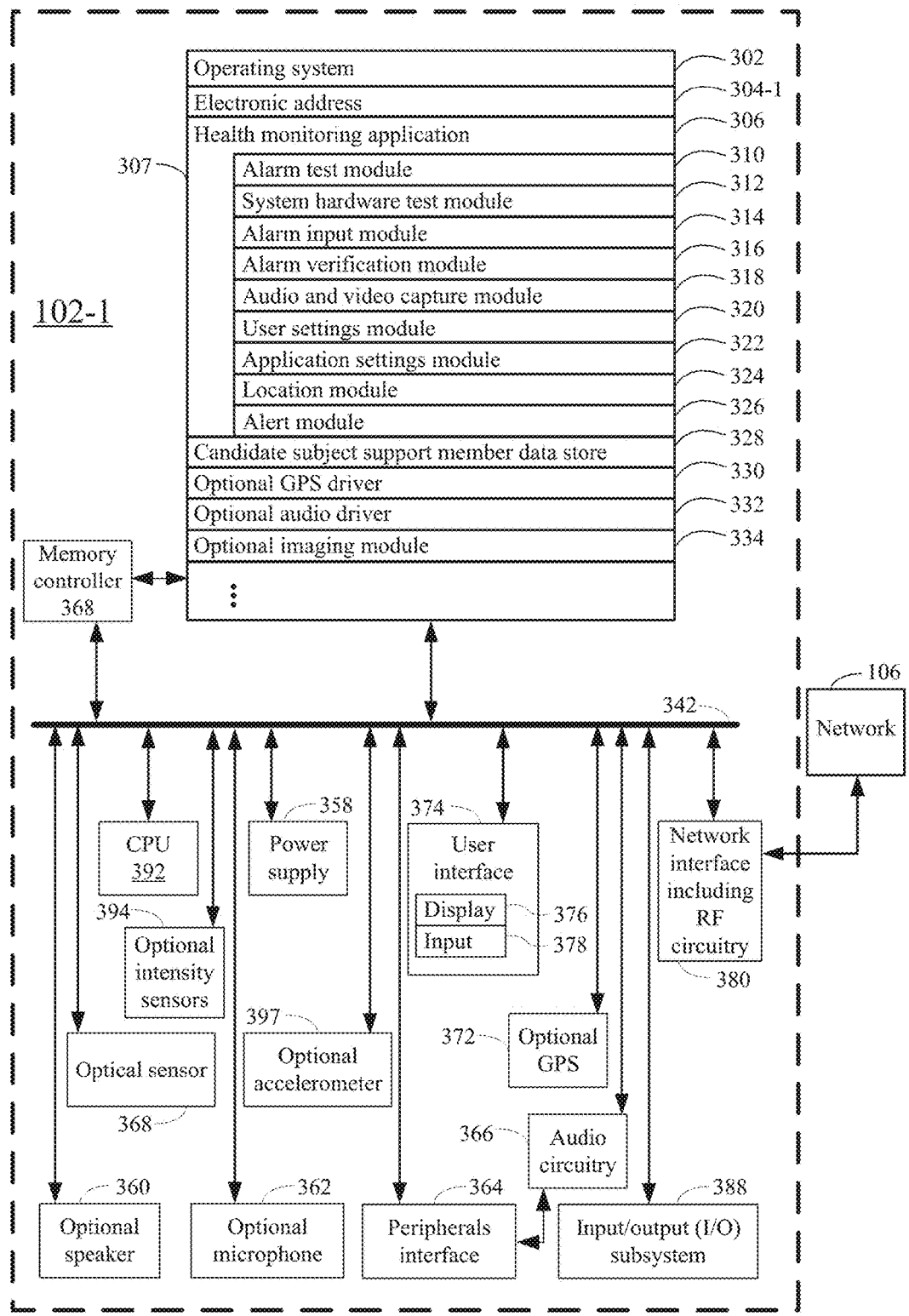
FIG. 3 illustrates modules and/or components of a health monitoring emergency support application according to an exemplary embodiment of the present disclosure.

A detailed description of a system 148 for providing a health monitoring and emergency support service in accordance with the present disclosure is described in conjunction with FIG. 1 through FIG. 3. As such, FIG. 1 through FIG. 3 collectively illustrate the topology of the system in accordance with the present disclosure. In the topology, there is a health monitoring and emergency support system 150 for receiving a plurality of data elements from a plurality of subjects and using these data elements to ascertain an alert trigger condition ("health monitoring and emergency support system 150") (FIG. 1 and FIG. 2), one or more health monitoring devices 102 associated with each subject (FIG. 1), and one or more remove devices associated with a support member of each subject (FIG. 1).

Referring to FIG. 1, the health monitoring and emergency support system 150 determines an alert trigger condition. To do the above, the health monitoring and emergency support system 150 receives data elements originating from one or health monitoring devices 102 that have been provided to a corresponding subject.

Each such data element comprises a condition of the health monitoring device 102 or a condition of the corresponding subject that was made by the health monitoring device 102.

In some embodiments the health monitoring and emergency support system 150 receives the data element wirelessly through radio-frequency signals. In some embodiments, such signals are in accordance with an 802.11 (WiFi), Bluetooth, or ZigBee standard.

In some embodiments, the health monitoring and emergency support system 150 receives the data elements directly. In some embodiments, the health monitoring and emergency support system 150 receives the data element from an auxiliary server (not shown) which analyzes the data, and passes the analyzed data to the health monitoring and emergency support system 150.

In some embodiments, the health monitoring and emergency support system 150 receives the data elements indirectly. For instance, in some embodiments, the device 102 is a measurement device (e.g., a glucose sensor) that shares a Bluetooth connection to a smart phone associated with the user. In such embodiments, the health monitoring device 102 passes a signal indicative of the health of the subject to the smart phone which, in turn, sends the signal to the health monitoring and emergency support system 150. In some such embodiments, the smart phone (not shown in FIG. 1) analysis the signal from the device 102 and only sends a data element to the health monitoring and emergency support system 150 when a predetermined threshold criterion has been satisfied (e.g., a sudden change in measured value associated with the health of the subject, a change in trend of a value associated with the health of the subject, etc.). In some such embodiments, there are any number of intermediate hops between the measurement device 102 and the health monitoring and emergency support system 150. For instance, after the device 102 has reported to a smart phone associated with the subject, the data may be sent to any number of intermediate servers for further analysis prior to sending to the health monitoring emergency support system 150.

In some embodiments, multiple health monitoring devices 102 are associated with a single subject. For instance, in some embodiments, one health monitoring device 102 monitors one physical attribute related to the health of the subject and another health monitoring device 102 measures a different physical attribute related to the health of the subject. For instance, one may measure the pulse of the subject while another measures the glucose levels of the subject. In such embodiments, any number of trend analysis or threshold alerts may be set up to monitor these measurements in order to determine whether to fire an alert to the health monitoring and emergency support system 150 in the form of a data element.

In some embodiments, a health monitoring device 102 includes an RFID tag and communicates the data element to the data the health monitoring and emergency support system 150 using RFID communication.

In some embodiments a health monitoring device 102 is a FREESTYLE LIBRE CGM by ABBOTT ("LIBRE") that makes a plurality of autonomous glucose measurements of a subject. The LIBRE allows calibration-free glucose measurements with an on-skin coin-sized sensor, which can send up to eight hours of data to a reader device (e.g., an intermediate data collection device not shown and/or the health monitoring and emergency support system 250) via near field communications, when brought close together. The LIBRE can be worn for fourteen days in all daily life activities. In some embodiments, the glucose measurements LIBRE or equivalent sensor autonomously takes glucose measurements from the subject at an interval rate of 5 minutes or less, 3 minutes or less, or 1 minute or less. In some embodiments, the glucose measurements are taken from the subject at an interval rate of 5 minutes or less, 3 minutes or less, or 1 minute or less, over a time period of a day or more, two days or more, a week or more, or two weeks or more.

In some embodiments, the health monitoring and emergency support system 150 is not proximate to the subject and/or does not have wireless capabilities or such wireless capabilities are not used for the purpose of acquiring data elements. In such embodiments, a communication network 106 may be used to communicate data elements from the health monitoring device 102 or remote device 104 to the health monitoring and emergency support system 150.

Examples of networks 106 include, but are not limited to, the World Wide Web (WWW), an intranet and/or a wireless network, such as a cellular telephone network, a wireless local area network (LAN) and/or a metropolitan area network (MAN), and other devices by wireless communication. The wireless communication optionally uses any of a plurality of communications standards, protocols and technologies, including but not limited to Global System for Mobile Communications (GSM), Enhanced Data GSM Environment (EDGE), high-speed downlink packet access (HSDPA), high-speed uplink packet access (HSUPA), Evolution, Data-Only (EV-DO), HSPA, HSPA+, Dual-Cell HSPA (DC-HSPDA), long term evolution (LTE), near field communication (NFC), wideband code division multiple access (W-CDMA), code division multiple access (CDMA), time division multiple access (TDMA), Bluetooth, Wireless Fidelity (Wi-Fi) (e.g., IEEE 802.11a, IEEE 802.11ac, IEEE 802.11ax, IEEE 802.11b, IEEE 802.11g and/or IEEE 802.11n), voice over Internet Protocol (VoIP), Wi-MAX, a protocol for e-mail (e.g., Internet message access protocol (IMAP) and/or post office protocol (POP)), instant messaging (e.g., extensible messaging and presence protocol (XMPP), Session Initiation Protocol for Instant Messaging and Presence Leveraging Extensions (SIMPLE), Instant Messaging and Presence Service (IMPS)), and/or Short Message Service (SMS), or any other suitable communication protocol, including communication protocols not yet developed as of the filing date of the present disclosure.

Of course, other topologies of the system 148 other than the one depicted in FIG. 1 are possible. For instance, rather than relying on a communications network 106, the one or more health monitoring devices 102 may wirelessly transmit information directly to the health monitoring system 250. Further, the health monitoring and emergency support system 150 may constitute a portable electronic device, a server computer, or in fact constitute several computers that are linked together in a network or be a virtual machine in a cloud computing context. As such, the exemplary topology shown in FIG. 1 merely serves to describe the features of an embodiment of the present disclosure in a manner that will be readily understood to one of skill in the art.

Referring to FIG. 2, in typical embodiments, the health monitoring and emergency support system 150 comprises one or more computers. For purposes of illustration in FIG.

2, the health monitoring and emergency support system 150 is represented as a single computer that includes all of the functionality for providing a health monitoring and emergency support system. However, the disclosure is not so limited. In some embodiments, the functionality for providing a health monitoring and support system is spread across any number of networked computers and or resides on each of several networked computers and or is hosted on one or more virtual machines at a remote location accessible across the communications network 106. One of skill in the art will appreciate that any of a wide array of different computer topologies are used for the application and all such topologies are within the scope of the present disclosure.

Turning to FIG. 2 with the foregoing in mind, an exemplary health monitoring and emergency support system 150 for providing a health monitoring and emergency support system comprises one or more processing units (CPU's) 274, a network or other communications interface 284, a memory 192 (e.g., random access memory), one or more magnetic disk storage and or persistent devices 290 optionally accessed by one or more controllers 288, one or more communication busses 112 for interconnecting the aforementioned components, a user interface 278, the user interface 278 including a display 282 and input 280 (e.g., keyboard, keypad, touch screen), and a power supply 276 for powering the aforementioned components. In some embodiments, data in memory 192 is seamlessly shared with non-volatile memory 290 using known computing techniques such as caching. In some embodiments, memory 192 and or memory 290 includes mass storage that is remotely located with respect to the central processing unit(s) 274. In other words, some data stored in memory 192 and/or memory 290 may in fact be hosted on computers that are external to the health monitoring and emergency support system 150 but that can be electronically accessed by the health monitoring and emergency support system 150 over an Internet, intranet, or other form of network or electronic cable (illustrated as element 106 in FIG. 2) using network interface 284.

In some embodiments, the memory 192 of the health monitoring and emergency support system 150 for providing emergency support stores:

an operating system 202 that includes procedures for handling various basic system services;

a polling module 206 that polls for alarm data elements from health monitoring devices 102 (e.g., in some embodiments each such alarm data element 208 including a notification that identifies the originating medical device 102, one or more medical device diagnostic conditions, and/or one or more medical device measurements);

a subject data store 210 that stores a plurality of subject records, where each respective subject record 212 in the plurality of subjects is for a corresponding subject and stores a subject contact information 214 and a subject support list 216 that includes contact information 220 of each remote device 104 associated with the corresponding subject, support member schedules 222 for providing an availability schedule of the support members, and a support member alarm type 224 which associates each support member 218 with one or more specific alarm types (e.g., specific emergency types).

In some embodiments the polling module 206 runs on native device frameworks, and is available for download onto the health monitoring and emergency support system 150 running an operating system 202 such as Android or iOS.

In some implementations, one or more of the above identified data elements or modules of the health monitoring and emergency support system 150 are stored in one or more of the previously described memory devices, and correspond to a set of instructions for performing a function described above. The above-identified data, modules or programs (e.g., sets of instructions) need not be implemented as separate software programs, procedures or modules, and thus various subsets of these modules may be combined or otherwise re-arranged in various implementations. In some implementations, the memory 192 and/or 290 optionally stores a subset of the modules and data structures identified above. Furthermore, in some embodiments the memory 192 and/or 290 stores additional modules and data structures not described above.

In some embodiments, a health monitoring device 102 and or remote device 104 are a smart phone (e.g., an iPHONE), laptop, tablet computer, desktop computer, or other form of electronic device (e.g., a gaming console).

FIG. 3 provides a description of a health monitoring device 102-1 that can be used with the instant disclosure. The health monitoring device 102 illustrated in FIG. 3 has one or more processing units (CPU's) 392, peripherals interface 364, memory controller 368, a network or other communications interface 380, a memory 307 (e.g., random access memory), a user interface 374, the user interface 374 including a display 376 and input 378 (e.g., keyboard, keypad, touch screen), an optional accelerometer 397, an optional GPS 372, optional audio circuitry 366, an optional speaker 360, an optional microphone 362, one or more optional intensity sensors 394, an optional input/output (I/O) subsystem 388, one or more optional optical sensors 368, one or more communication busses 342 for interconnecting the aforementioned components, and a power supply 358 for powering the aforementioned components.

In some embodiments, the input 378 is a touch-sensitive display, such as a touch-sensitive surface. In some embodiments, the user interface 374 includes one or more soft keyboard embodiments. The soft keyboard embodiments may include standard (QWERTY) and or non-standard configurations of symbols on the displayed icons.

The health monitoring device 102 illustrated in FIG. 3 optionally includes, in addition to accelerometer(s) 397, a magnetometer (not shown) and a GPS 372 (or GLONASS or other global navigation system) receiver for obtaining information concerning the location and orientation (e.g., portrait or landscape) of the health monitoring device 102 and or for determining an amount of physical exertion by the subject.

It should be appreciated that the health monitoring device 102 illustrated in FIG. 3 is only one example of a multi-function device that may be used for collecting data elements 206 from the health monitoring device(s) 102 of a corresponding subject in a plurality of subjects or the remote device(s) 104 of a corresponding support member in a plurality of support members, and that the health monitoring device 102 and or remote device 104 optionally has more or fewer components than shown, optionally combines two or more components, or optionally has a different configuration or arrangement of the components. In fact, as discussed above, in some embodiments, the data elements 208 are acquired by the health monitoring an emergency support system 150 directly from the health monitoring devices 102 and or remote device 104. The various components shown in FIG. 3 are implemented in hardware, software, firmware, or a combination thereof, including one or more signal processing and/or application specific integrated circuits.

Memory 307 of the health monitoring device 102 illustrated in FIG. 3 optionally includes high-speed random access memory and optionally also includes non-volatile memory, such as one or more magnetic disk storage devices, flash memory devices, or other non-volatile solid-state memory devices. Access to memory 307 by other components of the health monitoring device 102, such as CPU(s) 392 is, optionally, controlled by the memory controller 368.

In some embodiments, the data elements of FIG. 2 comprise a plurality of physiological measurements, and each such physiological measurement includes a measurement value. In some embodiments, the physiological measurement is body temperature of the subject. In some embodiments, the physiological measurement is a measurement of activity of the subject. In some embodiments, these physiological measurements serve as additional data, in addition to that provided by the health monitoring devices 102 that is found in acquired data elements associated with a subject. In some embodiments, these physiological measurements serve to verify or help to determine the condition of the corresponding subject in conjunction with the data from the health monitoring devices 102. In some embodiments, the optional accelerometer 317, optional GPS 319, and or magnetometer (not shown) of the health monitoring device 102 or such components is used to acquire such physiological measurements.

The peripherals interface 364 can be used to couple input and output peripherals of the device to CPU(s) 392 and memory 307. The one or more processors 392 run or execute various software programs and or sets of instructions stored in memory 307, such as the health monitoring application 306, to perform various functions for the health monitoring device 102 and to process data.

In some embodiments, the peripherals interface 364, CPU(s) 392, and memory controller 368 are, optionally, implemented on a single chip. In some other embodiments, they are implemented on separate chips.

RF (radio frequency) circuitry of network interface 380 receives and sends RF signals, also called electromagnetic signals. In some embodiments, the data elements are received using the present RF circuitry from one or more devices such as a health monitoring device 102 associated with a subject or remote device 104. In some embodiments, the RF circuitry 380 converts electrical signals to from electromagnetic signals and communicates with communications networks and other communications devices, health monitoring devices 102, remote devices 104, and or the health monitoring and emergency support system 150 via the electromagnetic signals. The RF circuitry 380 optionally includes well-known circuitry for performing these functions, including but not limited to an antenna system, an RF transceiver, one or more amplifiers, a tuner, one or more oscillators, a digital signal processor, a CODEC chipset, a subscriber identity module (SIM) card, memory, and so forth. RF circuitry 380 optionally communicates with the communication network 106. In some embodiments, the circuitry 380 does not include RF circuitry and, in fact, is connected to the network 106 through one or more hard wires (e.g., an optical cable, a coaxial cable, or the like).

In some embodiments, the audio circuitry 366, the optional speaker 360, and the optional microphone 362 provide an audio interface between the subject and the health monitoring device 102. The audio circuitry 366 receives audio data from the peripherals interface 364, converts the audio data to electrical signals, and transmits the electrical signals to the speaker 360. The speaker 360 converts the electrical signals to human-audible sound waves. The audio circuitry 366 also receives electrical signals converted by the microphone 362 from sound waves. The audio circuitry 366 converts the electrical signal to audio data and transmits the audio data to peripherals interface 364 for processing. Audio data is, optionally, retrieved from and or transmitted to the memory 307 and or the RF circuitry 380 by the peripherals interface 364.

In some embodiments, the power supply 358 optionally includes a power management system, one or more power sources (e.g., battery, alternating current (AC)), a recharging system, a power failure detection circuit, a power converter or inverter, a power status indicator (e.g., a light-emitting diode (LED)) and any other components associated with the generation, management and distribution of power in portable devices.

In some embodiments, the health monitoring device 102 optionally also includes one or more optical sensors 368. The optical sensor(s) 368 optionally include charge-coupled device (CCD) or complementary metal-oxide semiconductor (CMOS) phototransistors. The optical sensor(s) 368 receive light from the environment, projected through one or more lens, and converts the light to data representing an image. The optical sensor(s) 368 optionally capture still images and or video. In some embodiments, an optical sensor is located on the back of the health monitoring device 102, opposite the display 376 on the front of the health monitoring device 102, so that the input 378 is enabled for use as a viewfinder for still and or video image acquisition. In some embodiments, another optical sensor 368 is located on the front of the health monitoring device 102 so that the subject's image is obtained (e.g., to verify the health or condition of the subject, to determine the physical activity level of the subject, to help diagnose a subject's condition remotely, or to acquire visual physiological measurements of the subject, etc.).

As illustrated in FIG. 2, a health monitoring device preferably comprises an operating system 202 that includes procedures for handling various basic system services. The operating system 202 (e.g., iOS, DARWIN, RTXC, LINUX, UNIX, OS X, WINDOWS, or an embedded operating system such as VxWorks) includes various software components and or drivers for controlling and managing general system tasks (e.g., memory management, storage device control, power management, etc.) and facilitates communication between various hardware and software components.

In some embodiments the health monitoring device 102 is a smart phone. In other embodiments, the health monitoring device 102 is not a smart phone but rather is a tablet computer, desktop computer, emergency vehicle computer, or other form or wired or wireless networked device. In some embodiments, the health monitoring device 102 is worn by a corresponding subject.

In some embodiments, the health monitoring device 102 has any or all of the circuitry, hardware components, and software components found in the system depicted in FIG. 3. In the interest of brevity and clarity, only a few of the possible components of the health monitoring device 102 are shown to better emphasize the additional software modules that are installed on the health monitoring device 102.

An electronic address 304 is associated with each health monitoring device 102 in order to uniquely identify each device. Installed on the health monitoring device is the health monitoring application 306. In some embodiments, the health monitoring application comprises an alarm test module 310 configured to verify the usability of the alarm trigger, a system hardware test module 312 configured to verify the usability of the system hardware, an alarm input module 314 configured to allow a subject or support member to input an alarm, an audio and video capture module 318 configured to capture audio and video imagery from the heath monitoring device 102, a user's settings module 320 configured to allow a user to adjust personal settings and information, an application settings module 322 configured to enable a user to adjust the settings of the application, a location module 324 configured to register the user's GPS location, and an alert module 326 configured to provide the alarm.

Figure 4:
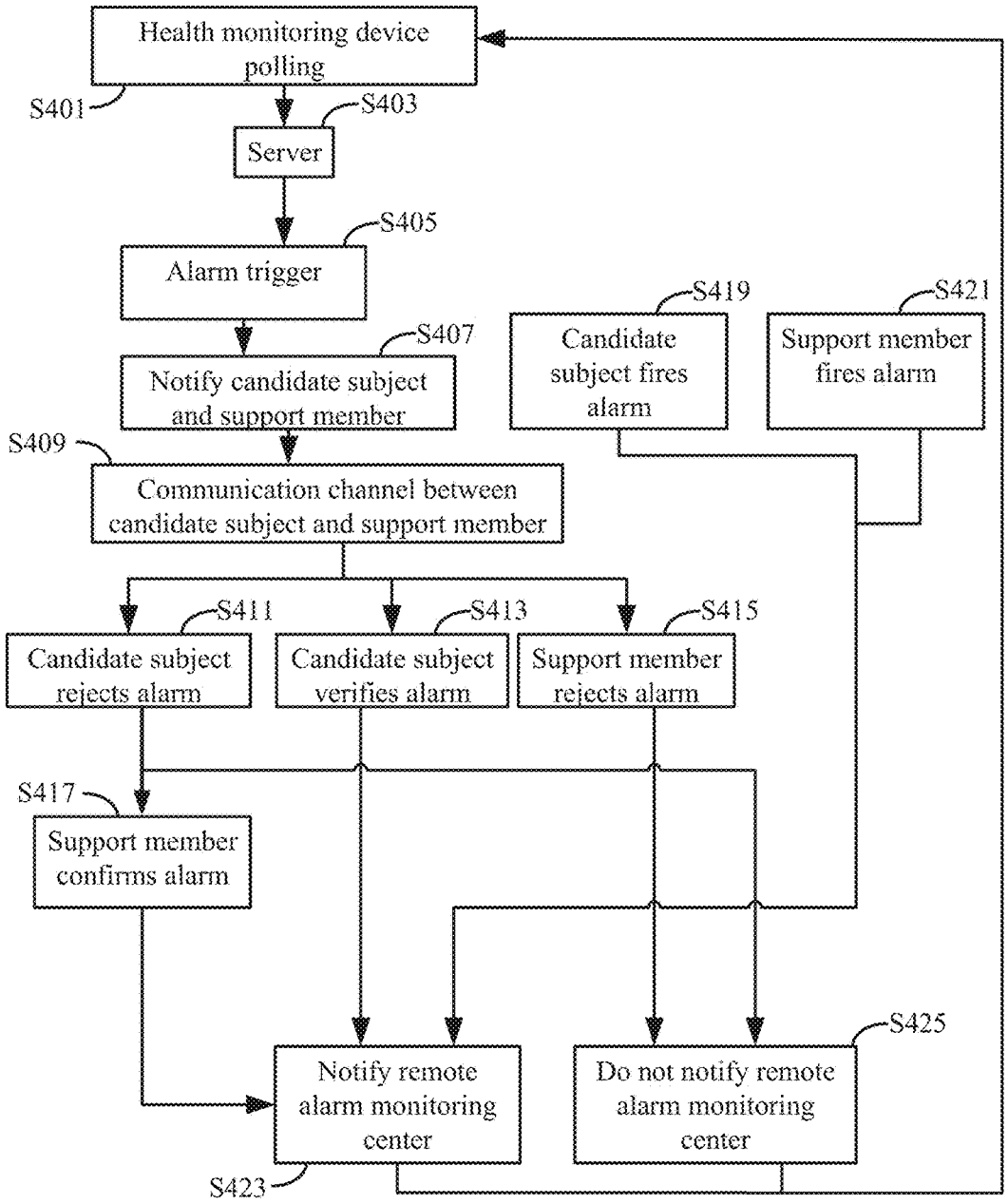
FIG. 4 provides a flow chart of processes and features of a computer system for a health monitoring emergency support system according to an exemplary embodiment of the present disclosure.

Now that details of a system 148 for providing a health monitoring and emergency support system have been disclosed, details regarding a flow chart of processes and features of the system, in accordance with an embodiment of the present disclosure, are disclosed with reference to FIG. 4.

Referring to FIG. 4, a health monitoring device 102-1 from a plurality of health monitoring devices 102 continuously polls for an alert trigger in the form of a respective data element (S401). In some embodiments, the alert trigger condition is a health event comprising any one of a change in temperature, a change in blood pressure, a heart attack, a detection of a slip or fall, a distress signal, an irregular heartbeat, or a change in blood glucose concentration. In some embodiments, the health monitoring device 102 is a diabetes glucose monitor, heart rate monitor, EKG monitor, wearable or the like.

In some embodiments, when the health monitoring device 102 registers an event or condition that may warrant an alert trigger, a respective data element regarding the alert trigger is forwarded to an auxiliary health data analytics server. In such embodiments, the respective data element comprises the alert trigger. In some such embodiments the data element comprises the GPS location of the subject and audio or video imagery captured from the health monitoring device 102.

In some embodiments, when the health monitoring device 102 registers an event or condition that may warrant an alert trigger, a respective data element regarding the alert trigger is forwarded to an auxiliary health data analytics server. In such embodiments, the auxiliary health data analytics server analyses the event or condition to determine if, in fact, an alert should be fired. For instance, in some embodiments, this analysis is performed by comparing the alert or condition to historical data associated with the subject that has been received from the subject in the past. In some embodiments, a trend analysis is performed on this historical data. In some embodiments, this trend analysis looks for the occurrence of a combination of conditions associated with the subject such as a blood pressure above a first predetermined threshold combined with a blood glucose level above a second predetermined threshold. As another example, this trend analysis looks for the occurrence of a combination of conditions associated with the subject such as candidate subject inactivity for greater than a predetermined period (as determined by the accelerometer of the device associated with the candidate subject) coupled with a biometric (e.g., blood pressure, blood glucose level, pulse, etc.) satisfying a threshold value.

In some embodiments the respective data element is sent to a gateway or software development kit (SDK) employed on a computing device for further analysis. In one such set up, there are two or more classes of devices associated with a candidate subject. The first class of devices constitutes measurement or data gather devices that measure a biometric of the candidate subject (e.g., on a recurring basis). These data gathering devices then send the data to the second class of device which analyzes the data (e.g., against trends or for the occurrence of a combination of conditions). For instance, such analysis comprises inferring a trend in measured values, some predetermined value extrema, or the like. In such embodiments, once the respective data element has been analyzed and an alert trigger condition is verified by the analysis, the data element is forwarded to a central command and control server (S403). Hereinafter, the respective data element may be called an alert trigger for simplicity and ease of understanding.

In some embodiments, the first class of devices (the measurement devices) and the second class of devices (the analysis devices) are the same devices. In one such embodiment, the first class of devices constitutes a smart phone that includes an accelerometer. The smart phone uses the accelerometer to track the motion of the subject. An SDK is installed on the smart phone. The SDK analyses the motion data looking for trends (e.g., no activity by the subject for longer than 20 minutes in the middle of the day).

Also, in some embodiments, the SDK can be distributed through a chain of computer systems, not just a single computer system. Thus, in such embodiments a first device associated with the subject, or several devices associated with the subject monitor one or more conditions of the subject and send data regarding these one or more conditions to another device for analysis (e.g., for trend discovery, for condition mapping, etc.). In so doing this analysis device may, in turn, invoke another analysis device in order to determine whether an alert should be fired. This calling process may in fact rely on any number of analysis computers in order to arrive at a final decision on whether to call an alert.

Once a respective data element is known to satisfy an alert trigger condition (or criteria), an alert is triggered (S405). Once an alert is triggered a notification is sent to the device associated with the subject and the respective device of each member 218 of the subject support list 216 (circle of support) of the subject (S407). In some embodiments, the support members to be notified from the subject support list 216 are elected by the predetermined support member alarm types and or the support members' availability (referring to 222 and 224 of FIG. 2B). For instance, a support member can elect to only receive notifications during predetermined times or for predetermined conditions or a combination of the two. In some embodiments, the notification to the electronic device of the subject comprises: a list of the members of the circle of support (subject support list 216) and corresponding phone number links (or other forms of electronic contact such as instant message address, E-mail address, or some combination of the above, referred to here as contact information 220), instructions on how to fire (activate) the medical alert when desired, and/or insurance information of the subject. In some embodiments, the notification to the electronic devices of the circle of support (CoS) comprises: the name of the subject and a description of the emergency healthcare condition, the phone number link (or other electronic communication link such as instant messaging address, E-mail address, etc.) of the subject, a list 216 of the circle of support members and their corresponding phone number links (or other electronic communication link such as instant messaging address, E-mail address, etc.), the names of the medical care specialists and corresponding phone number links of the subject, an alarm monitoring center phone number link and the medical alert account number of the subject, and/or the medical insurance information of the subject.

After a notification has been sent to the electronic devices of the subject and circle of support, a communication channel between the subject and corresponding support member is opened in some embodiments (S409). In some embodiments, the communication channel comprises a push-to-talk or open channel audio, text, and/or video channels between the device 102 associated with the candidate subject and the devices 104 associated with the subject support members. In some embodiments, the notify (S407) and the communicating (S409) are performed concurrently. In some embodiments, the communicating (S409) is omitted. In some embodiments, the notifications (S407, S409) comprise an audible alarm or alert. In typical embodiments, an emergency service such as 911 is not invoked even when the alert is verified either by the candidate subject or a support member 218.

When the alert trigger notification is sent to the electronic device 102 associated with the subject, the subject has the option to either reject (S411) or verify (S413) the alert trigger. When the candidate subject elects to manually verify the alert trigger, in some embodiments the subject does so through the use of the health monitoring application 306. In some such embodiments, the verification comprises the user pressing a button a predetermined number of times, thereby arming then sending the alert. In some such embodiments, the verification comprises the user pressing a button for a predetermined length of time and/or a predetermined number of times, thereby arming then sending the alert. In some such embodiments, the verification comprises the user entering in a verification code sequence (e.g., a passcode), thereby arming then sending the alert. In a further embodiment, the verification comprises the user speaking a voice command.

In some embodiments, the subject elects to automatically verify every alert trigger and omits manual verification. After an alert is verified, the subject has the option to interrupt or reject the alert. When an alert is interrupted, the alert is cancelled and the operations cease for the specific alert. In some embodiments, the subsequent interruption must be received within a predetermined time period of receiving the alert. In some embodiments, the interruption occurs when the user enters a password. In some embodiments, the interruption occurs when the user speaks a predetermined safe word.

In some embodiments, if the candidate subject verifies an alarm after cancelling an alarm, the verification is treated as a new alarm sequence that the user manually initiated. In such instances, process control passes to S419 and, autonomously without further human intervention, to S423, which is described in further detail below.

Returning to S413, when the candidate subject verifies the alert trigger, the alert is forwarded to an alarm monitoring center (S423). In some embodiments, the remote alarm monitoring center comprises a remote alarm company, a physician, a provider group, a hospital, a hospital network, a health insurance company, a pharmacy, a governmental body, a first responder business entity, or a prescribing clinician. In some embodiments, the forwarding of the alert comprises: the name of the candidate subject, the current location of the candidate subject (e.g., physical street address, GPS coordinates, etc.), the current phone number of the candidate subject, an emergency medical condition reference codes associated with the subject and/or reference codes pertaining to the medical condition, current medications taken by the candidate subject, allergies of the candidate subject, a name and contact information of a doctor of the candidate subject, details of emergency contact persons for the candidate subject and/or photographs of the candidate subject and/or any combination of the forgoing, and/or any combination of the forgoing in addition to other information. In typical embodiments, and in accordance with United States protocol, the alarm monitoring center calls the subject to verify the emergency. An unanswered call is considered a confirmation of an emergency. In some embodiments, when the emergency is confirmed (e.g., by calling the candidate subject) the alarm monitoring center dispatches an emergency responder to the subject's geo-location and/or current address and a notification is sent to the emergency responder comprising the subject's medical information from the alarm monitoring center.

When the subject rejects the alert trigger (S413), the remote alarm monitoring center is not notified (S425). However, when a support member verifies the alert after the subject has rejected the alert, the support member's verification takes precedence (S417). The support member verification (S417) is then forwarded to the alarm monitoring center and the above operations (S423) occur. When more than one support member is asked to verify the alert, precedence is take in order of receipt. For instance, when a first support member rejects an alert and a subsequent second support member verifies the alert, the subsequent command takes precedent and is forwarded to the remote monitoring center (S423). Likewise, when a first support member verifies an alert and a subsequent second support member rejects the alert, the subsequent command takes precedent and the remote monitoring center is not notified (S425). In some embodiments, the support member elects to automatically verify any alert triggers.

The support member has the option to reject the alert at his or her discrepancy (S415). For instance, when the support member suspects the subject has fired a false positive alert the support member can reject the alert. The alarm monitoring center is not notified (S425).

At any point in time, the subject can fire an alert directly to the remote alarm monitoring center (S419). At any point in time, the subject's support member(s) can fire an alert directly to the remote alarm monitoring center (S421).

In some embodiments, after the remote alarm monitoring center is or is not notified, the process is reinitiated beginning at S401. In some embodiments, after the remote alarm monitoring center is notified data continues to be extrapolated from the health monitoring device. In some embodiments, after the remote alarm monitoring center is notified, audio or video imagery are captured from the subject's health monitoring device. In some embodiments, after the remote alarm monitoring center is notified, the health monitoring device polling (S401) and subsequent steps are continuous carried out. In some embodiments, after the remote alarm monitoring center is notified, the subject's geo-location is periodically reported to the remote alarm monitoring center.

In some embodiments, the health monitoring device 102 can be remotely controlled to capture audio, video, or the like.

Referring to FIG. 5 to FIG. 8, a graphical user interface (GUI) is shown according to an exemplary embodiment of the present disclosure.

Figure 5:
FIG. 5 illustrates a user interface of a health monitoring emergency support system according to an exemplary embodiment of the present disclosure.

FIG. 5 illustrates a GUI of a panic alert 501 when sent to the electronic devices of the subject and support members. A panic alarm is typically an alarm that is manually fired by the subject. In the embodiment illustrated in FIG. 5, the user must press the button three times to send the alert; however, the present disclosure is not limited thereto. For instance, in some embodiments the user must press the button more than three times or in a predetermined sequence. As shown in FIG. 5, the GUI contains information 502 comprising the electronic device's geo-location, network signal strength, alert or alarm volume, and alert or alarm mute; however, the present disclosure is not limited thereto. For instance, in some embodiments, the information 502 comprises an emergency responders estimated arrival time (ETA), elapsed time since triggering the alarm, or the like.

Figure 6:
FIG. 6 illustrates a user interface of a health monitoring emergency support system according to an exemplary embodiment of the present disclosure.

FIG. 6 illustrates a GUI of a medical alert 601 when sent to the electronic devices of the subject and support members. A medical alarm is typically an alarm that is automatically sent for the subject. In the embodiment illustrated in FIG. 6, the user must press the button three times to send the alert; however, the present disclosure is not limited thereto. For instance, in some embodiments the user must press the button more than three times or in a predetermined sequence. As shown in FIG. 6, the GUI contains information 602 comprising the electronic device's geo-location, network signal strength, alert or alarm volume, and siren mute switch; however, the present disclosure is not limited thereto. In the embodiment illustrated in FIG. 6, the mute switch is active and network signal strength is lower than that of the information 502.

Figure 7:
FIG. 7 illustrates a user interface of a health monitoring emergency support system according to an exemplary embodiment of the present disclosure.
Figure 8:
FIG. 8 illustrates a user interface of a health monitoring emergency support system according to an exemplary embodiment of the present disclosure.

FIG. 7 illustrates an interruption method. In the embodiment illustrated in FIG. 7, the subject or support member must enter a predetermined password 701 within an allocated time period 702 in order to interrupt the alarm previously fired however, the present disclosure is not limited thereto. For instance, in some embodiments the user must press a button three times or more in a predetermined sequence, and in another embodiment the user must speak a predetermined safe word. FIG. 8 illustrates a GUI of another interruption method where the user must call a phone number 801 to interrupt the alarm.

Accordingly, a health monitoring and emergency support service according to an exemplary embodiment of the present disclosure achieves the advantages of streamlining the process of dispatching emergency responders, engaging a subject's circle of support, and supplying the emergency responders with critical patient medical information while minimizing or eliminating the number of false calls.

The foregoing descriptions of specific exemplary embodiments of the present invention have been presented for purposes of illustration and description. They are not intended to be exhaustive or to limit the invention to the precise forms disclosed, and obviously many modifications and variations are possible in light of the above teachings. The exemplary embodiments were chosen and described in order to explain certain principles of the invention and their practical application, to thereby enable others skilled in the art to make and utilize various alternatives and modifications thereof. It is intended that the scope of the invention be defined by the Claims appended hereto and their equivalents.

What is claimed is:

1. A computer system for providing a health monitoring and emergency support service to a plurality of subjects, the computer system comprising:
at a first computer comprising one or more first processors and a first memory, the first memory comprising first non-transitory instructions which, when executed by the one or more first processors, performs a first method comprising:
running a monitoring process, wherein, for each respective subject in the plurality of subjects, the monitoring process comprises:
(i) polling for a respective data element in a plurality of data elements from a corresponding health monitoring device in a plurality of health monitoring devices associated with the respective subject, and
(ii) initiating a first notification process for a candidate subject in the plurality of subjects when the respective data element satisfies an alarm trigger condition, wherein the first notification process, performed for the candidate subject in the plurality of subjects when the respective data element satisfies the alarm trigger condition, comprises:
communicating the data element or the alarm trigger condition to each remote device in a plurality of remote devices, wherein each remote device in the plurality of remote devices is associated with a respective support member in a plurality of support members, and wherein each respective support member is uniquely associated with the candidate subject;
communicating the data element or the alarm trigger condition to the corresponding health monitoring device associated with the candidate subject;
concurrently polling for a verification response from the plurality of remote devices and the health monitoring device associated with the candidate subject; and
responsive to receiving the verification response from either (i) any one or more remote devices in the plurality of remote devices or (ii) from and the health monitoring device associated with the candidate subject:
initiating a second notification process that notifies a remote alarm monitoring center about the alarm trigger condition and a current location of the candidate subject when the verification response satisfies a first condition, and
terminating the first notification process when the verification response satisfies a second condition without notifying the remote alarm monitoring center about the alarm trigger condition, wherein:
the first condition is satisfied in accordance with a determination that a most recently received verification response from one or more remote devices in the plurality of remote devices is a confirmation,
the first condition is satisfied in accordance with a determination that a most recently received verification response from the health monitoring device associated with the candidate subject is a confirmation, and
the second condition is satisfied in accordance with a determination that a most recently received verification response from either (i) any one or more remote devices in the plurality of remote devices or (ii) the health monitoring device associated with the candidate subject is a rejection.

2. The computer system of claim 1, wherein the corresponding health monitoring device is a smart phone device.

3. The computer system of claim 1, wherein the corresponding health monitoring device wirelessly transmits the respective data element to the computer system.

4. The computer system of claim 1, wherein the polling further comprises instructions for receiving an interrupt communication from the candidate subject, wherein when the interrupt communication from the candidate subject is received within a predetermined time period of receiving the respective data element for the candidate subject, the first notification process and the alarm trigger condition are cancelled.

5. The computer system of claim 4, wherein the predetermined time period is 15 seconds.

6. The computer system of claim 1, wherein the representative data element is inputted by the candidate subject using a push command at the health monitoring device associated with the candidate subject.

7. The computer system of claim 1, wherein when the representative data element satisfies the alarm trigger condition a timing of a predetermined time period is initiated, wherein:
the representative data element is terminated upon a lapse of the predetermined time period, or
the representative data element is inputted through a series of push commands by the candidate subject at the health monitoring device associated with the candidate subject during the predetermined time period.

8. The computer system of claim 1, wherein the respective data element includes global positioning system coordinates of the candidate subject and the communicating the data element or the alarm trigger condition to each remote device in the plurality of remote devices includes communicating the global positioning system coordinates of the candidate subject.

9. The computer system of claim 1, wherein the respective data element comprises recorded audio or video from the health monitoring device corresponding to the candidate subject and the communicating the data element or the alarm trigger condition to each remote device in the plurality of remote devices includes communicating the recorded audio or video of the candidate subject.

10. The computer system of claim 1, wherein the respective data element comprises live audio or video from the health monitoring device corresponding to the candidate subject and the communicating the data element or the alarm trigger condition to each remote device in the plurality of remote devices includes communicating the live audio or video of the candidate subject.

11. The computer system of claim 1, wherein the communicating the data element or the alarm trigger condition to each remote device in a plurality of remote devices occurs on a recurring basis.

12. The computer system of claim 1, wherein the communicating the data element or the alarm trigger condition to each remote device in a plurality of remote devices occurs on the recurring basis at a predetermined interval.

13. The computer system of claim 1, wherein the respective data element satisfies the alarm trigger condition when the respective data element comprises an audible alarm transmitted through the corresponding health monitoring device associated with the candidate subject.

14. The computer system of claim 1, wherein the plurality of support members uniquely associated with the candidate subject comprises a family member of the candidate subject or a friend of the candidate subject.

15. The computer system of claim 1, wherein each support member, in the plurality of support members serves as a recipient of the data element or the alarm trigger condition on a voluntary basis.

16. The computer system of claim 1, wherein the remote alarm company is a physician, a provider group, a hospital, a hospital network, a health insurance company, a pharmacy, a governmental body, a first responder business entity, or a prescribing clinician that receives the alarm trigger condition in the second notification process on a subscription basis with the candidate subject.

17. The computer system of claim 1, wherein
the first condition is validation by a respective support member of the need for emergency services for the candidate subject responsive to the communication of the data element or the alarm trigger condition, and
the second condition is affirmative validation by a respective support member of the absence of a need for emergency services for the candidate subject responsive to the communication of the data element or the alarm trigger condition.

18. The computer system of claim 1, wherein the notifying the remote alarm monitoring center further includes notifying the remote alarm monitoring of medial information related to the candidate subject.

19. The computer system of claim 1, wherein the further non-transitory instructions further include instructions for:
creating a communication channel between the candidate subject and each respective support member in the plurality of support members independent of a location of the respective support member responsive to the alarm trigger condition, wherein the communication channel allows for the candidate subject and a respective support member to directly communicate with each other.

20. A method for providing a health monitoring and emergency support service to a plurality of subjects, the method comprising:
at a first computer comprising one or more first processors and a first memory, the first memory comprising first non-transitory instructions which, when executed by the one or more first processors, performs a first method comprising:
running a monitoring process, wherein, for each respective subject in the plurality of subjects, the monitoring process comprises:
(i) polling for a respective data element in a plurality of data elements from a corresponding health monitoring device in a plurality of health monitoring devices associated with the respective subject, and
(ii) initiating a first notification process for a candidate subject in the plurality of subjects when the respective data element satisfies an alarm trigger condition, wherein the first notification process, performed for the candidate subject in the plurality of subjects when the respective data element satisfies the alarm trigger condition, comprises:
communicating the data element or the alarm trigger condition to each remote device in a plurality of remote devices, wherein each remote device in the plurality of remote devices is associated with a respective support member in a plurality of support members, and wherein each respective support member is uniquely associated with the candidate subject;
communicating the data element or the alarm trigger condition to the corresponding health monitoring device associated with the candidate subject;
concurrently polling for a verification response from the plurality of remote devices and the health monitoring device associated with the candidate subject; and
responsive to receiving the verification response from either (i) any one or more remote devices in the plurality of remote devices or (ii) from and the health monitoring device associated with the candidate subject:
initiating a second notification process that notifies a remote alarm monitoring center about the alarm trigger condition and a current location of the candidate subject when the verification response satisfies a first condition, and terminating the first notification process when the verification response satisfies a second condition without notifying the remote alarm monitoring center about the alarm trigger condition, wherein:
- the first condition is satisfied in accordance with a determination that a most recently received verification response from one or more remote devices in the plurality of remote devices is a confirmation,
- the first condition is satisfied in accordance with a determination that a most recently received verification response from the health monitoring device associated with the candidate subject is a confirmation, and
- the second condition is satisfied in accordance with a determination that a most recently received verification response from either (i) any one or more remote devices in the plurality of remote devices or (ii) the health monitoring device associated with the candidate subject is a rejection.

21. A non-transitory computer readable storage medium, wherein the non-transitory computer readable storage medium stores instructions, which when executed by a computer system, cause the computer system to perform a method for providing a health monitoring and emergency support service, the method comprising:
- at a first computer comprising one or more first processors and a first memory, the first memory comprising first non-transitory instructions which, when executed by the one or more first processors, performs a first method comprising:
- running a monitoring process, wherein, for each respective subject in the plurality of subjects, the monitoring process comprises:
  - (i) polling for a respective data element in a plurality of data elements from a corresponding health monitoring device in a plurality of health monitoring devices associated with the respective subject, and
  - (ii) initiating a first notification process for a candidate subject in the plurality of subjects when the respective data element satisfies an alarm trigger condition, wherein the first notification process, performed for the candidate subject in the plurality of subjects when the respective data element satisfies the alarm trigger condition, comprises:
    - communicating the data element or the alarm trigger condition to each remote device in a plurality of remote devices, wherein each remote device in the plurality of remote devices is associated with a respective support member in a plurality of support members, and wherein each respective support member is uniquely associated with the candidate subject;
    - communicating the data element or the alarm trigger condition to the corresponding health monitoring device associated with the candidate subject;
    - concurrently polling for a verification response from the plurality of remote devices and the health monitoring device associated with the candidate subject; and
    - responsive to receiving the verification response from either (i) any one or more remote devices in the plurality of remote devices or (ii) from and the health monitoring device associated with the candidate subject:
- initiating a second notification process that notifies a remote alarm monitoring center about the alarm trigger condition and a current location of the candidate subject when the verification response satisfies a first condition, and
- terminating the first notification process when the verification response satisfies a second condition without notifying the remote alarm monitoring center about the alarm trigger condition, wherein:
  - the first condition is satisfied in accordance with a determination that a most recently received verification response from one or more remote devices in the plurality of remote devices is a confirmation,
  - the first condition is satisfied in accordance with a determination that a most recently received verification response from the health monitoring device associated with the candidate subject is a confirmation, and
  - the second condition is satisfied in accordance with a determination that a most recently received verification response from either (i) any one or more remote devices in the plurality of remote devices or (ii) the health monitoring device associated with the candidate subject is a rejection.

\* \* \* \* \*

UNITED STATES PATENT AND TRADEMARK OFFICE
CERTIFICATE OF CORRECTION

PATENT NO. : 10,304,315 B2  
APPLICATION NO. : 15/618487  
DATED : May 28, 2019  
INVENTOR(S) : Newman et al.

Page 1 of 1

It is certified that error appears in the above-identified patent and that said Letters Patent is hereby corrected as shown below:

In the Claims

Column 19, Line 1-2, replace "representative" with -- respective --.
Column 19, Line 6, 9, 11, replace "representative" with -- respective -- (each occurrence).

Signed and Sealed this
Third Day of August, 2021

Drew Hirshfeld
*Performing the Functions and Duties of the*
*Under Secretary of Commerce for Intellectual Property and*
*Director of the United States Patent and Trademark Office*